United States Patent [19]
Small

[11] 3,968,792
[45] July 13, 1976

[54] STERILE TUBULAR DRAPE
[75] Inventor: Martin H. Small, Dallas, Tex.
[73] Assignee: Hydro-Med Products, Inc., Dallas, Tex.
[22] Filed: Apr. 4, 1975
[21] Appl. No.: 564,872

[52] U.S. Cl............................ 128/132 D; 128/165
[51] Int. Cl.² ......................................... A61F 13/00
[58] Field of Search............ 128/132 R, 132 D, 157, 128/165; 2/21

[56] References Cited
UNITED STATES PATENTS
| | | | |
|---|---|---|---|
| 2,522,842 | 9/1950 | Scholl | 128/157 X |
| 3,018,484 | 1/1962 | Koehn | 128/132 R |
| 3,136,417 | 6/1964 | Clinch | 128/132 R |

FOREIGN PATENTS OR APPLICATIONS
| | | | |
|---|---|---|---|
| 664,538 | 8/1938 | Germany | 2/21 |
| 1,026,044 | 3/1958 | Germany | 128/132 R |
| 528,068 | 6/1955 | Italy | 128/157 |

Primary Examiner—Lawrence W. Trapp
Attorney, Agent, or Firm—Jack A. Kanz

[57] ABSTRACT

Sterile tubular drapes of various diameter pre-cut to desired lengths, rolled for immediate application and packaged in sterile containers for ready use. The drapes may include pull straps rolled concentrically with the rolled wall of the drape to assist in rapid application of the drape to the patient's limb. The drapes may also include adhesive strips for attaching the drape to the patient.

9 Claims, 6 Drawing Figures

STERILE TUBULAR DRAPE

This invention relates to sterile drapes. More particularly, it relates to tubular orthopedic drapes of single or double-walled construction including pull straps for ease of application and packaged in sterile containers for immediate use.

During surgical operations it is common practice to cover all or most of the patient's body, particularly the portion surrounding the incision, with sterile drapes to avoid or minimize the risk of infection of the open wound by infectious materials carried on other portions of the body. To minimize the risk of self infection, the area surrounding the point of incision is thoroughly scrubbed and then the area surrounding the point of incision is draped with a sterile drape leaving only the area of incision exposed for the surgeon.

It is also a primary concern to the surgical team to minimize time in the operating room, both to conserve time of the surgical staff and to minimize use of the hospital and surgical facilities.

When performing surgical operations on a limb, such as an arm or a leg, it is common practice to encase the entire limb in a tubular drape commonly known as a stockinette. Tubular stockinette is generally provided in the form of large rolls of seamless tubular cotton fabric. The tubular stockinette is ordinarily 100% cotton woven in a seamless tubular structure in a stretch weave which permits the tubular structure to stretch in the radial direction but not in the axial direction. The tubular stockinette may be provided in various diameters such as 4 inch, commonly used for arms, and 6 inch, commonly used for legs. Various other dimensions are also commonly used. Likewise, the length may vary according to intented use.

In preparation for surgery the surgical staff ordinarily cuts the required number of lengths of stockinette from the supply roll and then must enclose one end by sewing or the like. The stockinette is then reversed so that the seam formed by closure of the end is internal. The stockinette is then sterilized and placed in a sterile container for use in the operating room. Frequently the entire supply roll is sterilized and placed in the operating room for use as needed. Accordingly, when a length of stockinette is required, the surgical nurse or assistant must remove the required length from the supply roll, close the end and reverse the tube; and then apply the stockinette to the limb while in the operating room. All this obviously consumes unnecessary time. Frequently, double-walled thicknesses of stockinette are required. Accordingly, the above-described operation must be duplicated and the second stockinette applied over the first stockinette, consuming further time of the operating staff.

In accordance with the present invention a sterile stockinette is provided in rolled pre-cut lengths and packaged in sterile containers for immediate use by the operating staff. The pre-packaged pre-rolled sterile stockinette thus eliminates the need for sizing, stitching, rolling and sterilization by the operating staff. Instead the sterile containers are placed in the operating room for ready use by the operating staff when required.

The pre-rolled, pre-packaged drapes of the invention may be either double-walled or single-walled as desired, and may also include pull straps concentrically rolled within the rolled walls of the stockinette itself to provide easy application of the stockinette to the patient; thus further minimizing preparation time required by the surgical staff. These and other features and advantages of the invention will become more readily understood from the following detailed description taken in connection with the appended claims and attached drawings in which:

Figure 1:
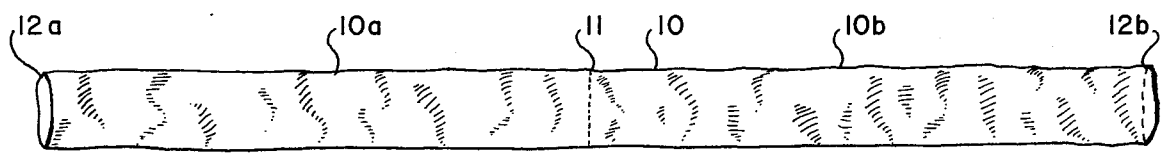
FIG. 1 is a pictorial view of a length of tubular stockinette open at both ends and closed at about the middle thereof.

Tubular orthopedic stockinette is commercially available in various forms. As used herein the term stockinette is used to describe any of the various commercially available woven tubular materials which are generally supplied in rolls of continuous length. To provide a double-walled stockinette in accordance with the invention, a suitable length of tubular stockinette (approximately twice the length of the desired double-walled stockinette) is cut from the stock roll. As indicated in FIG. 1 a closure 11 is formed at about the middle of the length of stockinette 10. The closure 11 may be formed by simply sewing or stitching laterally across the full width of the stockinette 10; thereby forming two stockinettes 10a and 10b, each having an open end 12a and 12b and a mutual closed end joined at closure 11.

Figure 2:
FIG. 2 is a pictorial view of the stockinette of FIG. 1 with one section of the stockinette reversed and drawn over the other section to form a double-walled stockinette.

To form a double-walled stockinette, one of the stockinettes 10b is reversed and drawn over the other stockinette 10a as shown in FIG. 2. When stockinette 10b is reversed and drawn over stockinette 10a the closure 11 forms a closed end and the open ends 12a and 12b form the open end of the stockinette. It should be observed that in this embodiment the stockinette 10 is double-walled and has no seam at the closed end 11, either on the inside or the outside thereof.

To package the stockinette for sterilizaton and use the open ends 12a and 12b are flared outwardly and the walls of the stockinettes jointly rolled toward the closed end 11 forming a single rolled body in the form of a doughnut. When the stockinette is completely rolled to the closed end, the closed end 11 forms a web across the center of the doughnut. The rolled stockinette may then be packaged in a suitable disposable container, such as polyethylene or the like, for terminal sterilization. If the container is hermetically sealed, the stockinette remains sterile and ready for immediate use.

Figure 3:
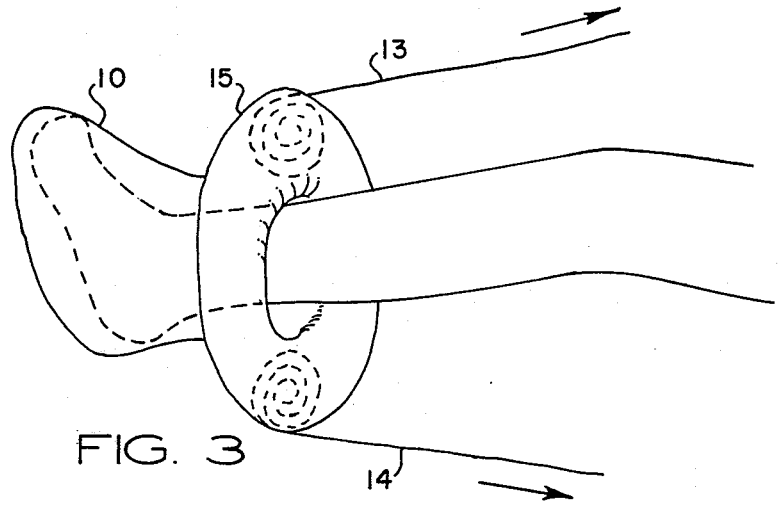
FIG. 3 is a pictorial view of a stockinette of the invention including pull straps concentrically rolled within the walls of the stockinette and illustrating application of the stockinette to a patient's leg.

To assist in application of the rolled orthopedic drape to the patient's limb, pull straps may be rolled concentrically with the walls of the stockinette. As illustrated in FIG. 3, straps 13 and 14 may be positioned on the outside of the stockinette 10 when the stockinette is in the unrolled condition. The straps 13 and 14 need not be attached to the stockinette but should be substantially the same length as the stockinette 10. When the open ends 12a and 12b are curled outwardly from the center of the stockinette, the ends of the straps 13 and 14 are likewise curled outwardly and, as the stockinette is rolled, the straps 13 and 14 are rolled concentrically within the rolled stockinette wall. Accordingly, when the stockinette is rolled to the closed end 11, the ends of straps 13 and 14 extend from the center of the doughnut-shaped roll.

To apply the stockinette to the patient's limb, the closed end of the stockinette opposite the side from which the straps 13 and 14 extend is placed on the end of the patient's appendage and the straps 13 and 14 pulled toward the patient's body as indicated by the arrows in FIG. 3. As the straps are pulled the roll 15 is unrolled, thereby pulling the walls of the stockinette onto the patient's appendage. When the end of the roll is reached the straps are free and may be discarded. It will thus be observed that the stockinette may be applied rapidly to the patient's limb smoothly and rapidly thus eliminating the need for smoothing the stretching the stockinette as it is applied.

In many instances the patient's limb is surgically cleaned and the surgical drape applied thereto prior to the incision. Accordingly, the surgeon cuts through the surgical drape immediately prior to making the incision in the patient. In such cases it is important that the surgical drape remains firmly in place during the following surgical operation.

Figure 4:
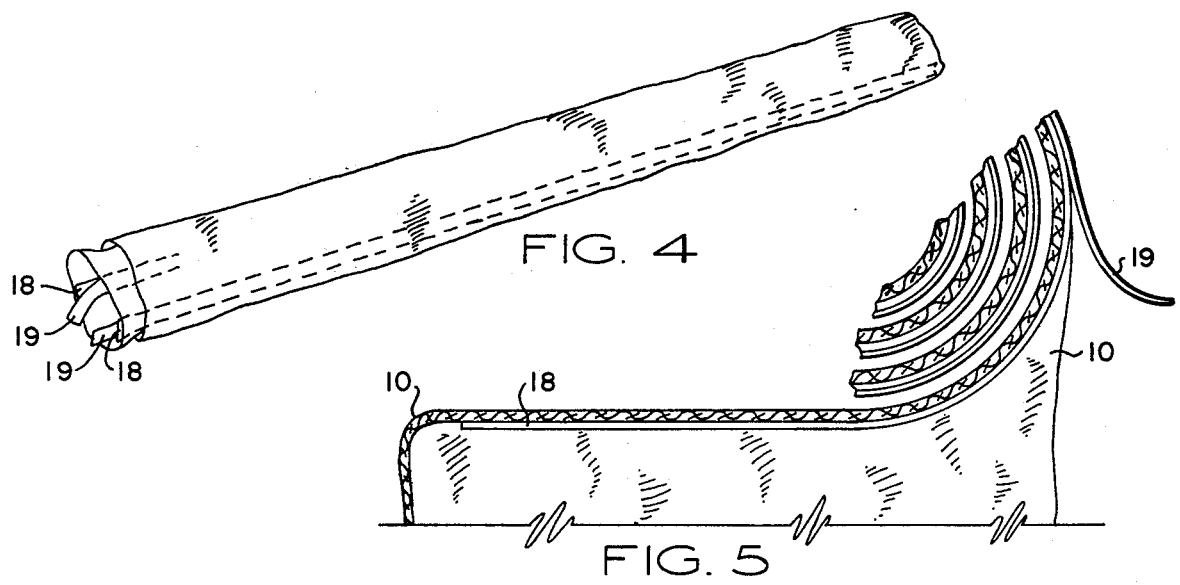
FIG. 4 is a pictorial view of an alternative embodiment of the stockinette of the invention including double-sided adhesive strips attached to the interior wall with a backing material to protect the internal adhesive face and serving as a pull strap for application of the stockinette.

To assist in retaining the drape in position during the surgery, a tubular stockinette may be provided with one or more adhesive strips on the internal surface thereof which adhere directly to the patient's limb. The adhesive material is preferably combined with the pull strap as indicated in FIGS. 4, 5 and 6.

The adhesive material may be used with either single-walled or double-walled drapes as described hereinabove. In the preferred embodiment the tubular stockinette is formed as described above and a pair of adhesive strips 18 affixed to the internal surface of the stockinette. For convenience the adhesive strips may be affixed to the external surface of the stockinette in the unrolled condition and the entire stockinette then reversed so that the adhesive strips are affixed to the internal surface. In the preferred embodiment the adhesive strips comprise a double-sided adhesive strip such as a web of material having adhesive on both sides thereof, and a protective backing 19 on one side thereof. Accordingly, the adhesive strips are placed on the outside of the stockinette and affixed thereto. The stockinette is then reversed so that the protective backing of the adhesive strips are on the internal surface of the stockinette and the protective backing 19 prevents the opposite side of the strips from adhering to the stockinette. The stockinette is then rolled, curving the open ends outwardly so that the adhesive strip and protective backing 19 is concentrically rolled with the walls of the stockinette. Application of the tubular drape so formed as illustrated in the sectional drawing of FIG. 5.

Figure 5:
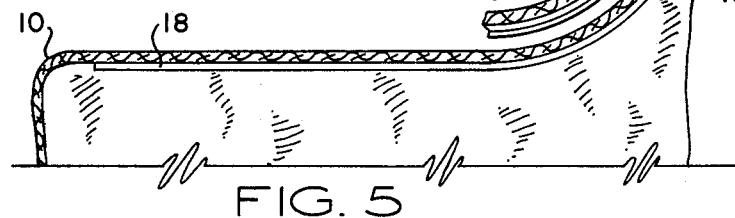
FIG. 5 is a sectional view of a partially unrolled stockinette illustrating the application of the stockinette of FIG. 4 to the patient's limb.

As shown in FIG. 5 the stockinette 10 is applied to the patient's limb and the backing 19 is used as a pull strap. Accordingly, as the backing is removed from the adhesive strip 18, the roll 15 unrolls and the adhesive material 18 is progressively applied directly to the patient's limb. The stockinette is simultaneously unrolled and applied to the patient's limb, the adhesive strip 18 thus holding the drape in place.

Figure 6:
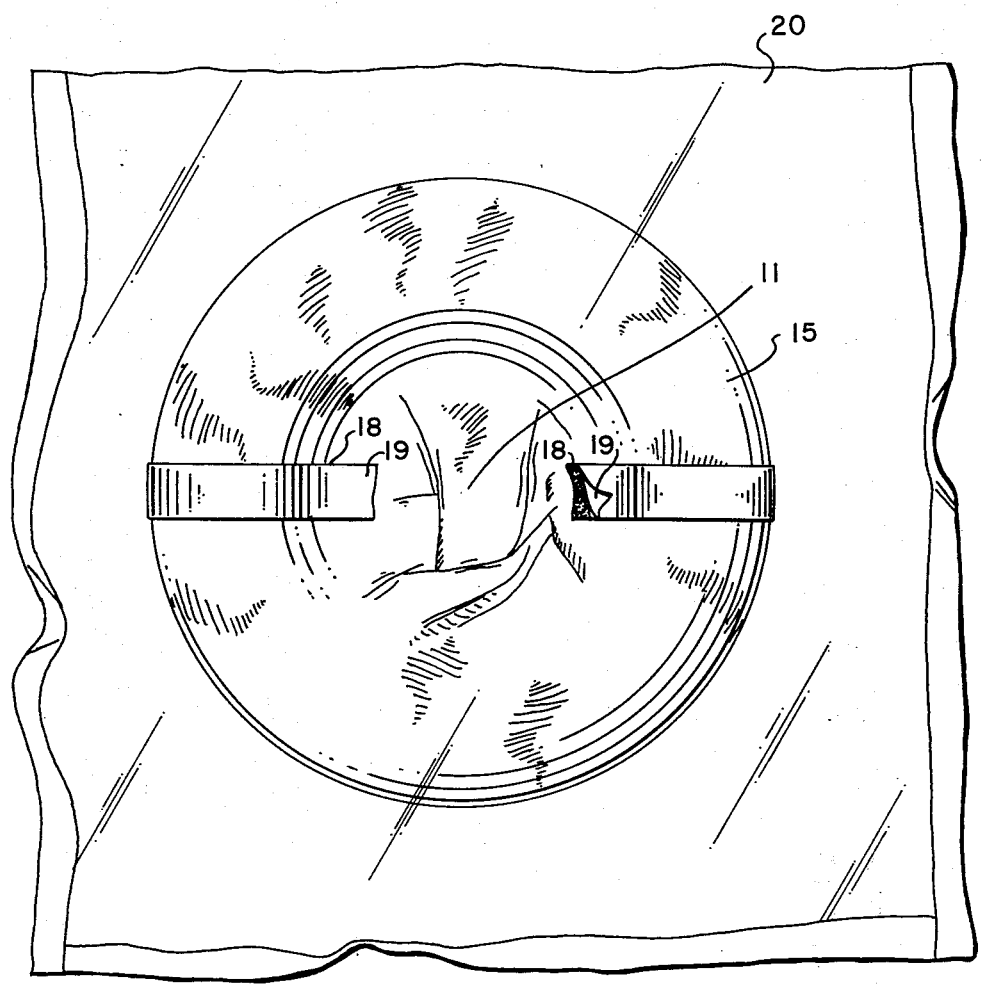
FIG. 6 is a top plan view of the stockinette of FIG. 4 rolled and packaged in a sterile container.

The packaged product of the preferred embodiment is illustrated in FIG. 6 ready for use. As illustrated in FIG. 6 the stockinette is in the form of a doughnut-shaped roll with the enclosed end 11 forming a web across the center of the doughnut. In the embodiment illustrated, the pull straps incorporate two double-faced adhesive strips 18 diametrically opposed on opposite sides of the interior wall of the stockinette; each having one face adherently fixed to the stockinette. The ends of the strips 18 and backing 19 terminate at the center of the doughnut. The rolled stockinette is enclosed within a disposable container such as polyethylene bag 20 or other means such as a vacumn sealed bag or the like. The entire package may then be sterilized by conventional terminal sterilization techniques and, since the bag is hermetically sealed, the stockinette remains in sterile condition until the bag is opened.

Since the pre-packaged pre-cut stockinette described is maintained in sterile condition until the bag is opened, the surgical staff need not consume time or effort in sterilization of the stockinette. Instead a supply of the stockinettes of the invention may be placed in the operating room ready and convenient for use whenever desired. For use the preparation team merely opens the bag, places the closed end 11 over the end of the patient's limb, and pulls the ends of the backing strips 19 to apply the stockinette to the full length of the affected limb of the patient. Accordingly, vast savings of time are realized. Furthermore, since the stockinettes are fully prepared and rolled prior to opening the bag, time need not be consumed in cutting and rolling the stockinette in the operating room. It should also be noted that double-walled stockinettes as described hereinabove may be readily and conveniently supplied without any seam or the like to extend from the outer end of the enclosed end; nor are bulky seams enclosed within the inside of the stockinette.

As an added feature the pull straps 13, 14 or the backing 19 used in connection with different diameter stockinettes may be different colors. Accordingly, the color of the pull strap may be used to indicate size. It will be apparent that such color codes may be used to indicate length, width or both length and width, thus facilitating immediate recognition of the desired drape and further increasing the efficiency of operating staff time.

It should be understood that although the invention has been described with particular reference to specific embodiments thereof, the forms of the invention shown and described in detail are to be taken as preferred embodiments of same, and that various changes and modifications may be resorted to without departing from the spirit and scope of the invention as defined by the appended claims.

What is claimed is:

1. A sterile drape comprising a tubular stockinette open at both ends and closed at about the middle to form two tubular stockinettes each having an open end and a mutual closed end, one of said tubular stockinettes reversed and drawn over the other tubular stockinette to form a double-walled tubular stockinette having one open end and one closed end; the double-walled tubular stockinette having the open end thereof folded outwardly from the center thereof and rolled toward the closed end.

2. A sterile drape as defined in claim 1 including at least one elongated strap of substantially the same length as said double-walled tubular stockinette positioned on the outer wall thereof and concentrically rolled within the rolled wall of said tubular stockinette.

3. A sterile drape as defined in claim 1 including a hermetically sealed container enclosing said sterile drape to maintain said drape sterile until said container is opened.

4. A sterile drape comprising a tubular stockinette having an open end and a closed end; at least one elongated strap affixed to the internal wall of said tubular stockinette and carrying an adhesive on the surface of said strap facing toward the interior of said tubular stockinette, the open end of said tubular stockinette curled outwardly from the center thereof and rolled toward the closed end including said elongated strap concentrically within the rolled tubular stockinette.

5. The sterile drape as defined in claim 4 wherein the color of said elongated strap indicates the dimensions of said stockinette.

6. The sterile drape as defined in claim 4 including a hermetically sealed disposable container enclosing said sterile drape and maintaining said drape in sterile condition until said container is opened.

7. A sterile drape comprising a tubular stockinette having an open end and a closed end; at least one elongated strap extending along the length of the outside of said tubular stockinette, the open end of said tubular stockinette curled outwardly from the center thereof and rolled toward the closed end including said elongated strap concentrically within the rolled tubular stockinette, the color of said elongated strap indicating the dimensions of said stockinette.

8. The sterile drape as defined in claim 7 including a hermetically sealed disposable container enclosing said sterile drape and maintaining said drape in sterile condition until said container is opened.

9. The sterile drape defined in claim 5 wherein said elongated strap comprises a flexible medium with adhesive surfaces on opposite sides thereof, one adhesive surface adhering to the internal wall of said tubular stockinette and the other adhesive surface carrying a removable backing.

* * * * *

UNITED STATES PATENT OFFICE
CERTIFICATE OF CORRECTION

Patent No. 3,968,792   Dated July 13, 1976

Inventor(s) Martin H. Small

It is certified that error appears in the above-identified patent and that said Letters Patent are hereby corrected as shown below:

Column 1, line 36, "intented should read --- intended ---.
Column 3, line 25, "the", second occurrence, should read --- and ---.

Signed and Sealed this

Twenty-sixth Day of October 1976

[SEAL]

*Attest:*

RUTH C. MASON
*Attesting Officer*

C. MARSHALL DANN
*Commissioner of Patents and Trademarks*